United States Patent [19]
Bock et al.

[11] Patent Number: 4,563,451
[45] Date of Patent: Jan. 7, 1986

[54] QUINAZOLINO-1,4-BENZODIAZEPIN-5,13-DIONES

[75] Inventors: Mark G. Bock; Roger M. Freidinger, both of Hatfield; Ben E. Evans; George D. Hartman, both of Lansdale, all of Pa.

[73] Assignee: Merck & Co., Inc., Rahway, N.J.

[21] Appl. No.: 695,108

[22] Filed: Jan. 25, 1985

[51] Int. Cl.$^4$ .................. A61K 31/55; C07D 403/14
[52] U.S. Cl. .............................. 514/219; 260/239.3 P
[58] Field of Search ................. 260/239.3 P; 424/251; 514/219

[56] References Cited

U.S. PATENT DOCUMENTS 3,651,046  3/1972  Derieg et al. ................ 260/239.3 P
4,187,306  2/1980  Mayer et al. ................ 260/239.3 P Primary Examiner—Robert T. Bond
Attorney, Agent, or Firm—Richard A. Elder; Hesna J. Pfeiffer; Daniel T. Szura

[57] ABSTRACT

Novel quinazolino-1,4-benzodiazepin-5,13-diones, which have been found to be antagonists of the function of cholecystokinins (CCK), to the preparation of these compounds from compounds prepared by aerobic fermentation of certain *Aspergillus alliaceus* strains, and to the use of these compounds to antagonize the function of CCK, which antagonism is useful, e.g., for the treatment and prevention of disorders of the gastrointestinal, central nervous and appetite-regulatory systems of mammals, especially of humans.

17 Claims, No Drawings

QUINAZOLINO-1,4-BENZODIAZEPIN-5,13-DIONES

The present invention is directed to novel quinazolino-1,4-benzodiazepin-5,13-diones, which have been found to be antagonists of the function of cholecystokinins (CCK), to the preparation of these compounds, and to the use of these compounds to antagonize the function of CCK, which antagonism is useful, e.g., for the treatment and prevention of disorders of the gastrointestinal, central nervous and appetite regulatory systems of mammals, especially of humans.

BACKGROUND OF THE INVENTION

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed., Raven Press, N.Y., 1980, p. 169), and include, e.g., CCK-33, a neuropeptide of thirty-three amino acids and its carboxyl terminal octapeptide, CCK-8. These molecules are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotransmitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists to CCK have been useful for preventing or treating CCK-related disorders of the gastrointestinal, central nervous and appetite-regulatory systems of mammals, especially of humans. Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G161 (1982) and P. Robberecht et al., *Mol. Pharmacol.*, 17, 268 (1980)). The second class comprises peptide antagonists which are C-terminal fragments and analogs of CCK, of which both shorter (Boc—Met—Asp—Phe—NH₂, Met—Asp—Phe—NH₂) and longer (Cbz—Tyr(SO₃H)—Met—Gly—Trp—Met—Asp—NH₂) C-terminal fragments of CCK can function as CCK-antagonists, according to recent structure-function studies (see, R. T. Jensen et al., *Biochim. Biophys. Acta.*, 757, 250 (1983), and M. Spanarkel et al., *J. Biol. Chem.*, 258, 6746 (1983)). Then, the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC₅₀: generally $10^{-4}$M, but down to $10^{-6}$M in the case of the peptides) and the peptide CCK-antagonists have substantial stability and absorption problems.

The compound, 7β-((2,3,9,9Aα-tetrahydro-9α-hydroxy-2-(2-methylpropyl)-3-oxo-1H-imidazo-(1,2-A)-indol-9-yl)-methyl)quinazolino(3,2-A)(1,4)benzodiazepin-5,13-(6H,7H)dione of the formula (I):

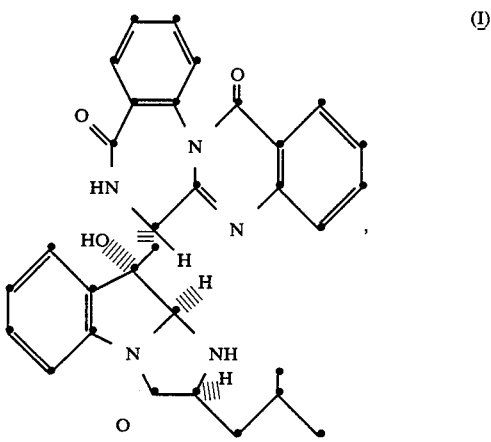

which is produced in a controlled aerobic fermentation of a strain of *Aspergillus alliaceus* Thom and Church, preferably strain ATCC No. 20655 or strain ATCC No. 20656, as disclosed in U.S. application Ser. No. 509,883, filed Sept. 20, 1983 now U.S. Pat. No. 4,530,790 (which is incorporated herein by reference), has been shown to be a CCK-antagonist.

It was an object of this invention to identify substances which demonstrate improved potency versus the compound, 7β-((2,3,9,9Aα-tetrahydro-9α-hydroxy-2-(2-methylpropyl)-3-oxo-1H-imidazo(1,2-A)indol-9-yl)-methyl)quinazolino(3,2-A)(1,4)benzodiazepin-5,13-(6H,7H)dione, in antagonizing the function of cholecystokinins in disease states in mammals, especially in humans. It was another object of this invention to develop a method of preparing these novel cholecystokinin-antagonists. It was also an object of this invention to develop a method of antagonizing the function of cholecystokinins in disease states in mammals. It was still a further object of this invention to develop an improved method of preventing or treating disorders of the gastrointestinal, central nervous and appetite regulatory systems of mammals, especially of humans.

SUMMARY OF THE INVENTION

The instant invention is directed to certain quinazolino-1,4-benzodiazepin-5,13-diones, which have been found to be antagonists of the function of cholecystokinins (CCK), to the preparation of these compounds from compounds prepared by aerobic fermentation of certain *Aspergillus alliaceus* strains, and to the use of these compounds in the treatment and prevention of disorders of the gastrointestinal, central nervous and appetite regulatory systems of mammals, especially of humans.

DETAILED DESCRIPTION OF THE INVENTION

The quinazolino-1,4-benzodiazepin-5,13-diones of this invention are compounds of the formula (II):

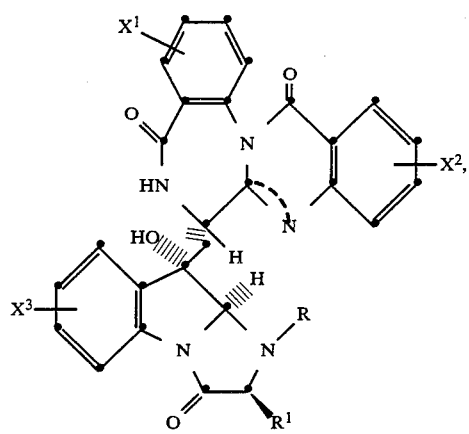

wherein:

$X^1$, $X^2$ and $X^3$ are independently H, Br, Cl, F, OH, $C_1$-$C_4$—alkyl, O—$C_1$-$C_4$—alkyl or

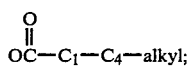

R is H, when the variable bond is a single bond; $C_1$-$C_8$—straight- or branched-chain or cyclic alkyl;

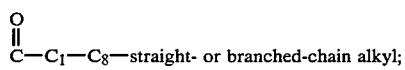

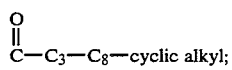

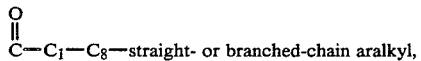

where the aryl is, for example, phenyl or naphthyl, which is unsubstituted or is monosubstituted on the aromatic ring by Br, Cl, F, OH, O—$C_1$-$C_4$—alkyl or

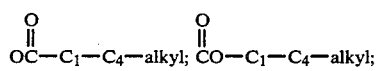

where the substituent is Br, Cl, F, OH, O—$C_1$-$C_4$—alkyl or

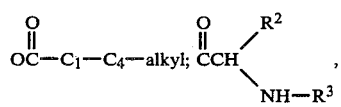

where $R^2$ is H; $C_1$-$C_4$—straight- or branched-chain alkyl; $CH_2$—unsubstituted or monosubstituted phenyl, wherein the substituent is Br, Cl, F, OH, O—$C_1$-$C_4$—alkyl or (II)

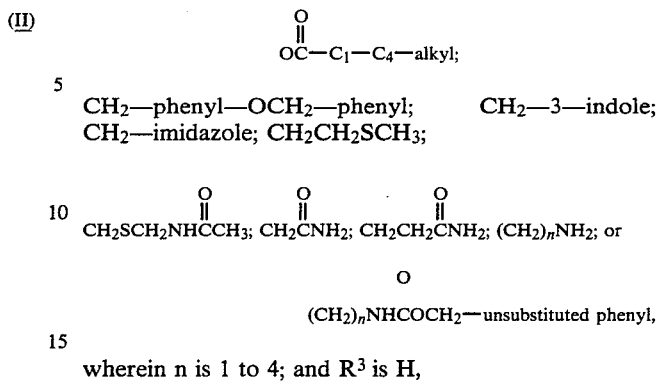

$CH_2$—phenyl—$OCH_2$—phenyl;  $CH_2$—3—indole; $CH_2$—imidazole; $CH_2CH_2SCH_3$;

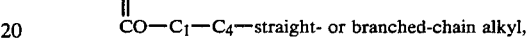

(CH$_2$)$_n$NHCOCH$_2$—unsubstituted phenyl, wherein n is 1 to 4; and $R^3$ is H,

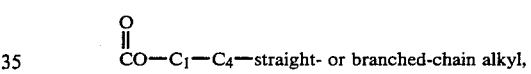

or

 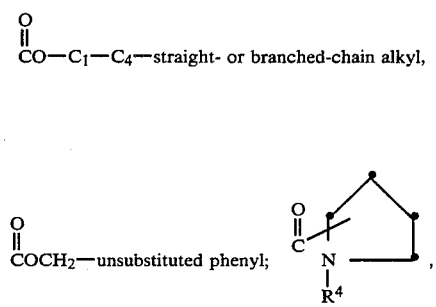

where $R^4$ is H,

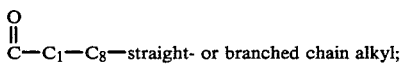

or

$OR^5$, where $R^5$ is $C_1$-$C_8$—straight- or branched chain or cyclic alkyl;

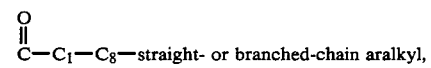

where the aryl is, for example, phenyl or naphthyl, which is unsubstituted or is monosubstituted on the aromatic ring by Br, Cl, F, OH, O—$C_1$-$C_4$—alkyl or

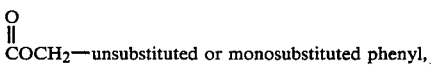

where the substituent is Br, Cl, F, OH, $C_1$-$C_4$—alkyl, O—$C_1$-$C_4$—alkyl or

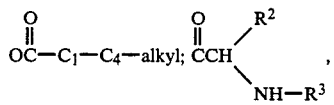

where $R^2$ and $R^3$ are as defined above; or

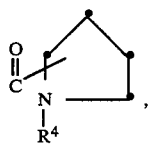

where $R^4$ is as defined above; or OH, when the variable bond is a single bond;

$R^1$ is H, $C_1$-$C_4$—straight- or branched-chain alkyl, including methyl, ethyl, propyl, isopropyl, butyl, isobutyl and t-butyl; $CH_2R^6$, where $R^6$ is hydroxy—$C_1$-$C_4$—alkyl or $CH_2SCH_3$; or unsubstituted or monosubstituted phenyl, where the substituent is OH or $OSO_3H$; and is a variable (saturated [single] or unsaturated [double]) bond, or pharmaceutically-acceptable salts of these compounds.

Preferred compounds of formula II, according to the instant invention, include those in which $X^1$, $X_2$ and $X^3$ are H; R is H, OH (when the variable bond is a single bond), $CH_2CH_3$, $CH_2CH_2CH_2$—unsubstituted phenyl,

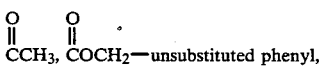

$CCH_3$, $COCH_2$—unsubstituted phenyl,

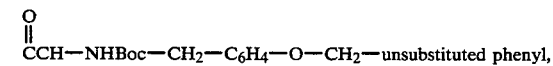

$CCH$—NHBoc—$CH_2$—$C_6H_4$—O—$CH_2$—unsubstituted phenyl,

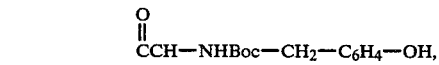

$CCH$—NHBoc—$CH_2$—$C_6H_4$—OH,

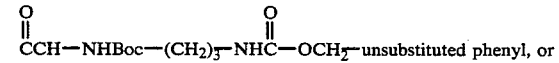

$CCH$—NHBoc—$(CH_2)_3$—NHC—$OCH_2$—unsubstituted phenyl, or $CCH$—NHBoc—$(CH_2)_4$—NHC—$OCH_2$—unsubstituted phenyl, wherein Boc is tert.-butyloxycarbonyl; and $R^1$ is $CH_2CH(CH_3)_2$, and the pharmaceutically-acceptable salts thereof. These preferred compounds include 7,7a-dihydro-7-[(2,3,9,9Aα-tetrahydro-9α-hydroxy-2-(2-methylpropyl)-3-oxo-1H-imidazo(1,2-A)indol-9-yl)methyl]quinazolino(3,2-A)(1,4)benzazepin-5,13-(6H,8H)dione; 7-[(1-acetyl-2,3,9,9Aα-tetrahydro-9α-hydroxy-2-(2-methylpropyl)-3-oxo-1H-imidazo(1,2-A)indol-9-yl)methyl]quinazolino(3,2-A)-1,4-benzodiazepin-5,13-(6H,7H)-dione; 7-[(1-ethyl-2,3,9,9 Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinazolino(3,2-A)-1,4-benzazepin-5H,13-dione; phenylmethyl 2,3,9,9Aα-tetrahydro-9α-hydroxy-2-(2-methylpropyl)-(3-oxo-9-[(5,6,7,13-tetrahydro-5,13-dioxoquinazolino-(3,2-A)-1,4-benzazepin-7-yl)methyl]-1H-imidazo-(1,2-A)indole-1-carboxylate; 7,7α-dihydro-7-[(2,3,9,9Aα-tetrahydro-1,9α-dihydroxy-2-(2-methylpropyl)-3-oxo-1H-imidazo(1,2-A)-indol-9-yl)methyl]quinazolino(3,2-A)-1,4-benzodiazepin-5,13-(6H,7H)-dione; 7-[1-(3-phenylpropyl)-2,3,-9,9Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinzolino(3,2-A)-1,4-benzazepin-5H,13-dione; 7-{{1-[N-((1,1-dimethylethoxy)carbonyl)-o-phenylmethyltyrosyl]-2,3,9,9Aα-tetrahydro-9α-hydroxy-2-(2-methylpropyl)-3-oxo-1H-imidazo(1,2-A)-indol-9-yl}methyl}quinazolino(3,2-A)-1,4-benzodiazepin-5,13-(6H,7H)-dione; 7-{{1-[2-((1,1-dimethylethoxy)carbonyl)amino-3-(4-hydroxyphenyl)propanoyl]-2,3,9,9Aα-tetrahydro-9α-hydroxy-2-(2-methylpropyl)-3-oxo-1H-imidazo(1,2-A)-indol-9-yl}methyl}quinazolino-(3,2-A)-1,4-benzodiazepin-5,13-(6H,7H)dione; 7-{{1-[2-((1,1-dimethylethoxy)carbonyl)amino-6-(Phenylmethyloxycarbonyl)aminohexanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)dione; 7-{{1-[2-((1,1-dimethylethoxy)carbonyl)amino-5-(phenylmethyloxycarbonyl)aminopentanoyl]-2,3,9,9Aα-tetrahydro-9α-hydroxy-2-(2-methylropyl)-3-oxo-1H-imidazo(1,2-A)indol-9-yl}methyl}quinazolino(3,2-A)-1,4-benzodiazepin-5,13-(6H,7H)dione; and 7-{{1-[2-((1,1-dimethylethoxy)carbonyl)amino-5-(phenylmethyloxycarbonyl)aminopentanoyl]-2,3,9,9Aα-tetrahydro-9α-hydroxy-2-(2-methylpropyl)-3-oxo-1H-imidazo(1,2-A)indol-9-yl}methyl}-6,7,7A,8-tetrahydro-5H,13-quinazolino(3,2-A)-1,4-benzodiazepin-5H,13-dione.

Particularly preferred compounds according to the instant invention include those in which $X^1$, $X^2$ and $X^3$ are H; R is H, OH, $CH_2CH_3$ or $CH_2CH_2CH_2$—unsubstituted phenyl; $R^1$ is $CH_2CH(CH_3)_2$; and the variable bond is a single bond, and pharmaceutically-acceptable salts thereof. These particularly preferred compounds include 7,7a-dihydro-7-[(2,3,9,9Aα-tetrahydro-9α-hydroxy-2-(2-methylpropyl)-3-oxo-1H-imidazo(1,2-A)-indol-9-yl)methyl]quinazolino-(3,2-a)(1,4)benzazepin-5,13-(6H,8H)dione; 7,7α-dihydro-7-[(2,3,9,9Aα-tetrahydro-1,9α-dihydroxy-2-(2-methylpropyl)-3-oxo-1H-imidazo(1,2-A)-indol-9-yl)-methyl]-quinazolino(3,2-A)-1,4-benzodiazepine-5,13-(6H,7H)-dione; 7-[(1-ethyl-2-,3,9,9Aα-tetra-hydro-9α-hydroxy-2-(2-methylpropyl)-3-oxo-1H-imidazo-(1,2-A)indol-9-yl)methyl]-6,7,7A,8-tetrahydro-5H,13H-quinazolino(3,2-A)-1,4-benzazepin-5H,13-dione; and 7-[(1-(3-phenylpropyl)-2,3,9,9Aα-tetrahydro-9α-hydroxy-2-(2-methylpropyl)-3-oxo-1H-imidazo-(1,2-A)indol-9-yl)-methyl]-6,7,7A,8-tetrahydro-5H,13H-quinazolino(3,2-A)-1,4-benzazepin-5H,13-dione.

The pharmaceutically-acceptable salts of the compounds of the instant invention include the conventional soluble, non-toxic salts of the compounds of this invention formed, for example, from non-toxic inorganic acids or bases or from organic acids and amines. Such conventional non-toxic salts include those derived from inorganic acids, such as hydrochloric, hydrobromic, sulfuric, sulfamic, phosphoric or nitric, or from very strong organic acids, such as ethane disulfonic, trifluoroacetic or isethionic acids and the like; or, if $R^1$=$CH_2$— monosubstituted phenyl where the substituent is $OSO_3H$, the salts derived from inorganic bases such as lithium hydroxide, sodium hydroxide, potassium hydroxide, calcium hydroxide, magnesium hydroxide, and the like; or the salts prepared from organic amines, such as trimethyl, triethyl, diisopropylethyl amines and the like.
Compounds according to formula II of the instant invention and salts thereof may be produced by one or more of four schemes, viz:
SCHEME 1
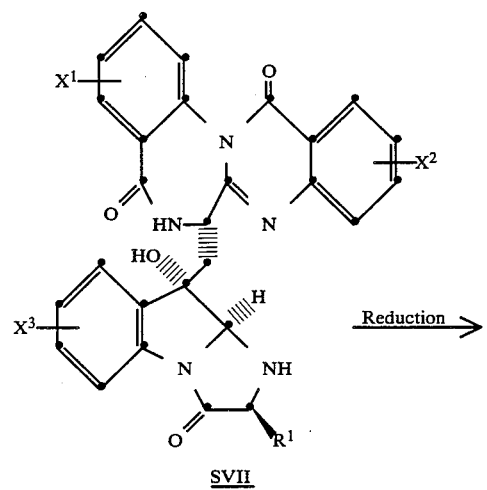
SVII
Reduction →
-continued
SCHEME 1
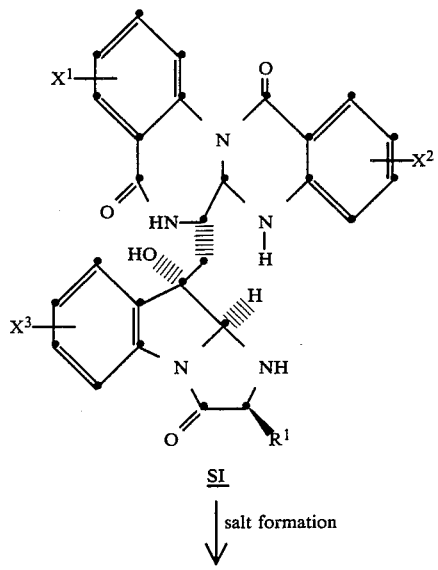
SI
↓ salt formation
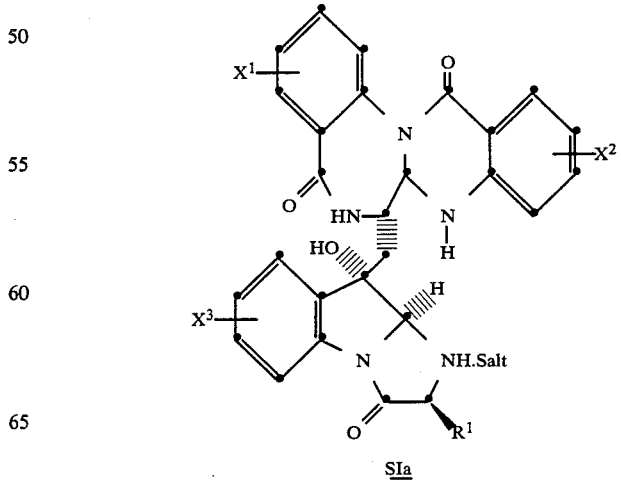
SIa SCHEME 2
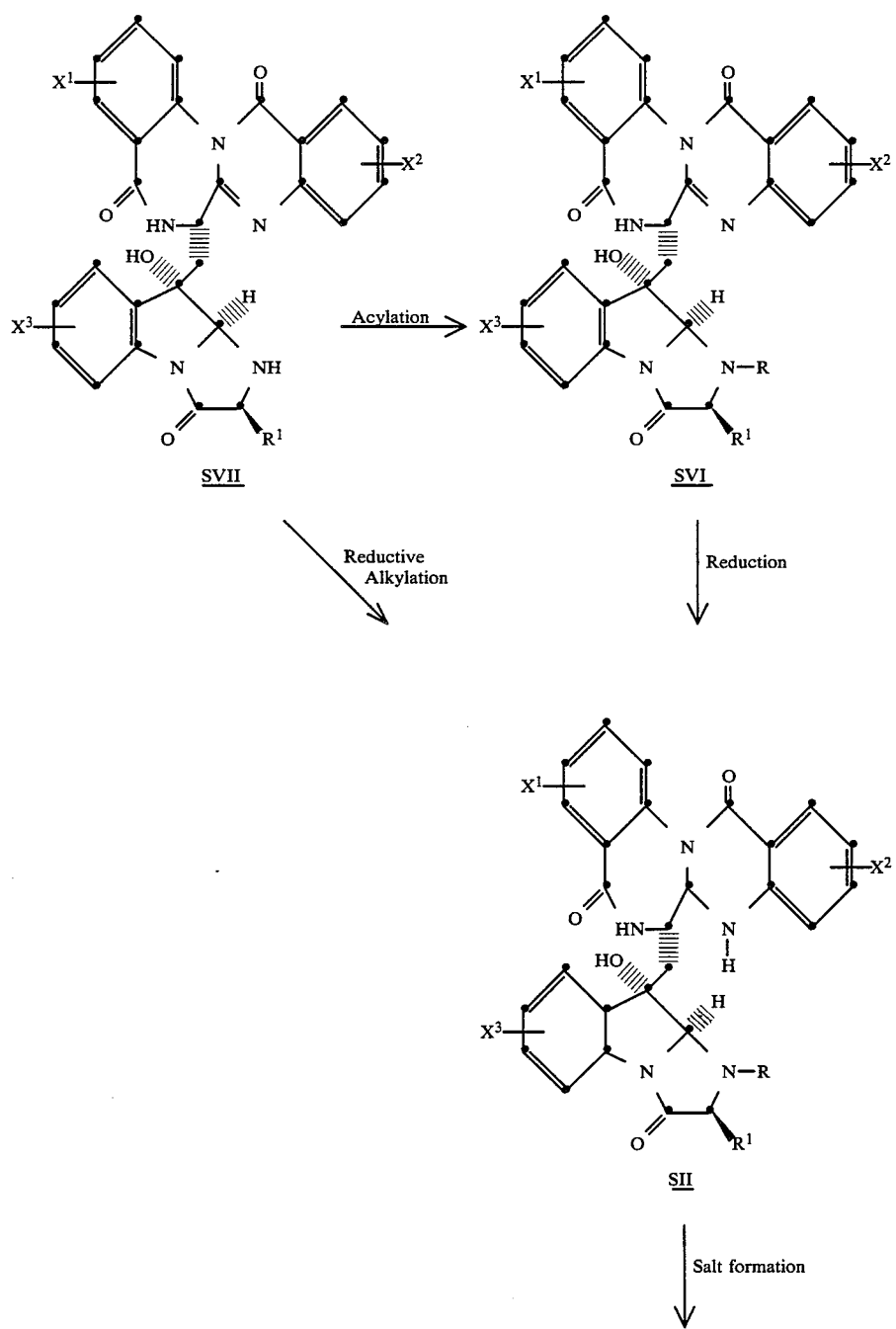

SCHEME 2
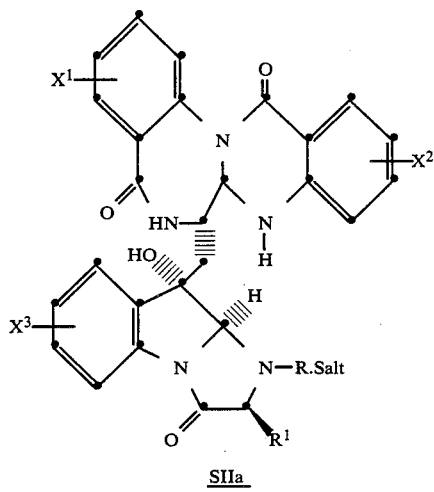
SIIa
SCHEME 3
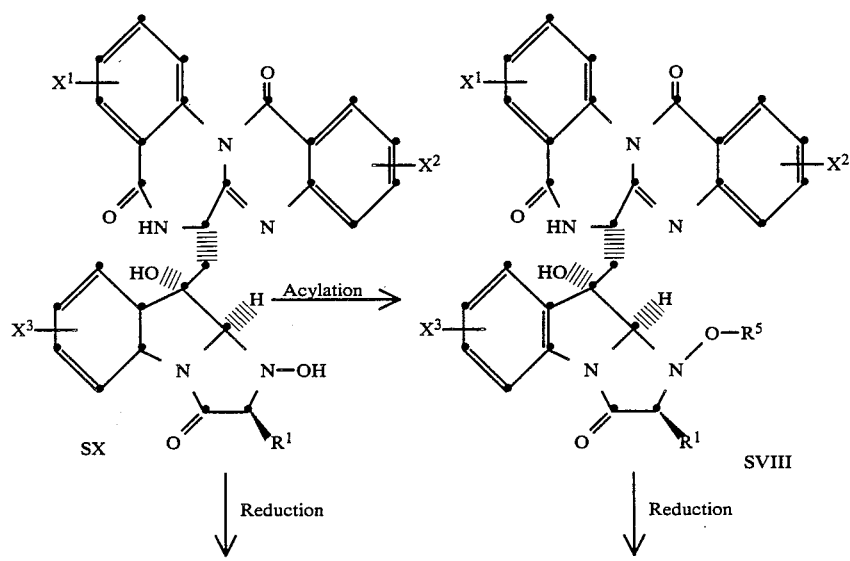

SCHEME 3
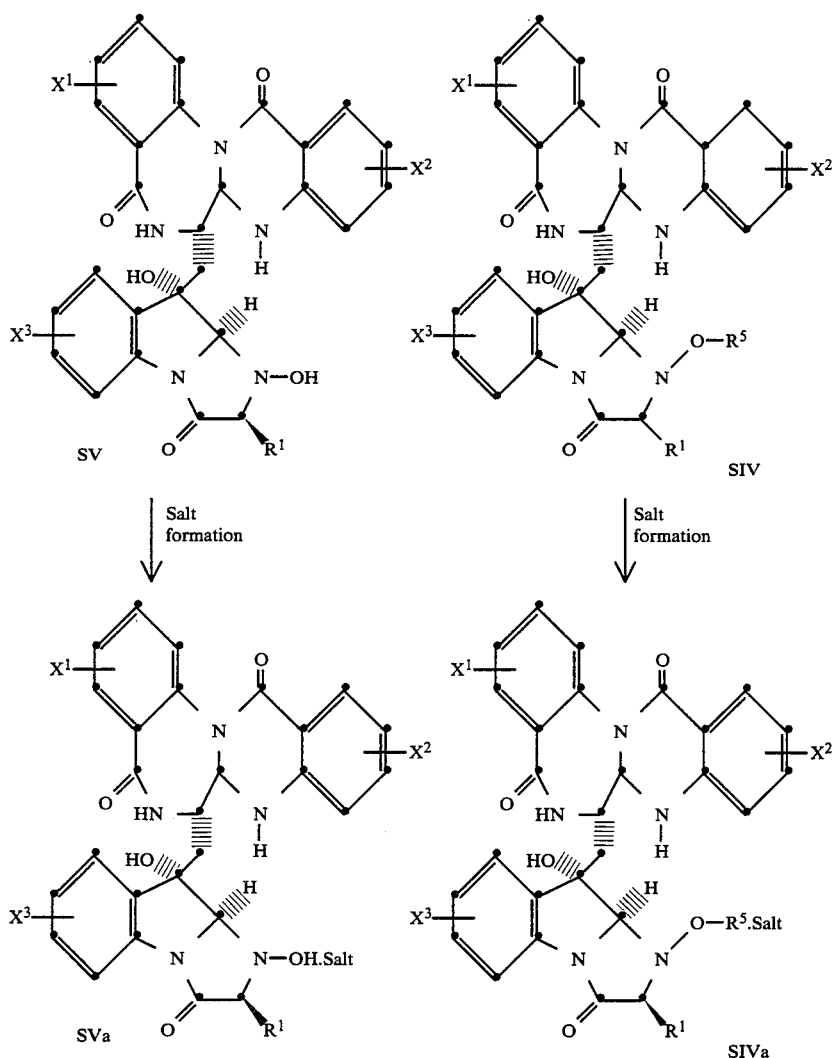
SCHEME 4
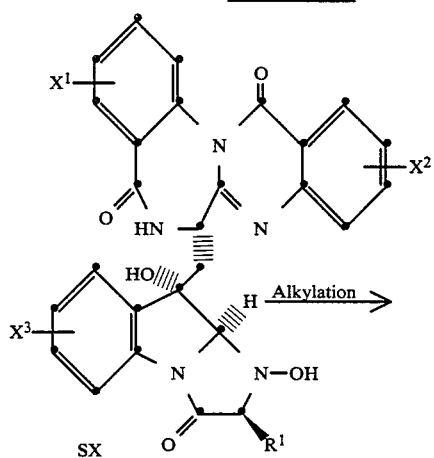
-continued
SCHEME 4
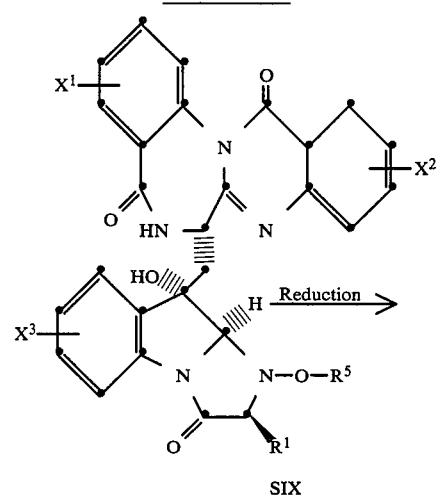

-continued
SCHEME 4

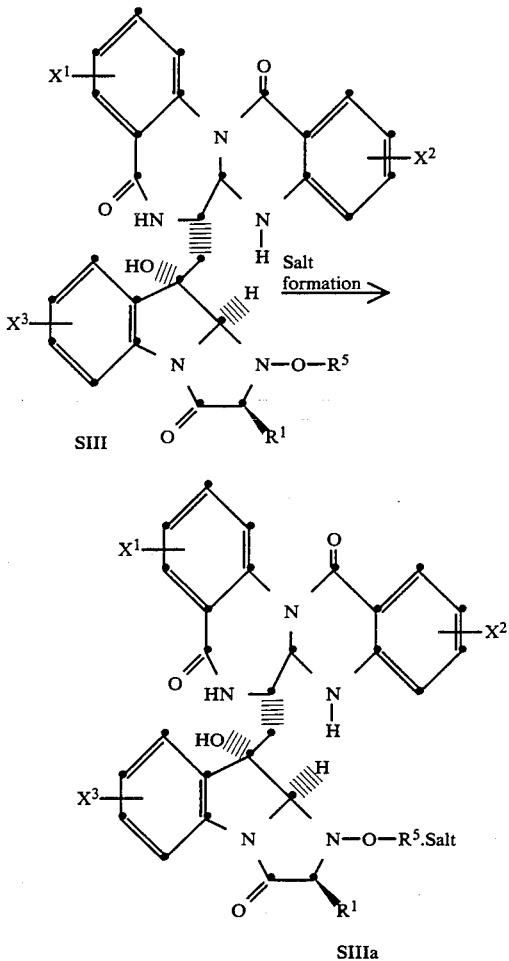

According to Scheme 1, compounds of the general formula SI may be obtained by reducing compounds of the general formula SVII by reacting a compound of formula SVII in a protic solvent, such as water, acetic acid, trifluoroacetic acid, methanol, ethanol and the like, or in an aprotic solvent, like tetrahydrofuran, with a reducing agent, such as sodium cyanoborohydride or lithium, sodium, or potassium borohydride, in a suitable medium, such as acetic acid, trifluoroacetic acid or ethanol, at from −40° C. to the boiling point of the solvent, for from 5 minutes to 10 hours. Preferably, the reaction is carried out in an acidic medium, such as acetic acid or trifluoroacetic acid, at 15° C. for 0.5 hours with sodium cyanoborohydride.

Compounds of the general formula SI may then subsequently be converted to their corresponding salts of formula SIa. This may be accomplished by conventional chemical means by suspending compounds of formula SI in a solvent, such as water, methanol, ethanol, ethyl acetate, tetrahydrofuran, or other suitable organic solvent or combinations of solvents, and treating the resulting reaction mixture with stoichiometric amounts of or with an excess of the desired salt-forming inorganic or organic acid or base. Examples of appropriate salt-forming inorganic bases include alkali or alkaline earth metal hydroxides, such as sodium, lithium, potassium, calcium or magnesium hydroxides, or potassium carbonate, while appropriate organic bases include tertiary amines, such as triethylamine, dibenzylethylenediamine, diisopropylethylamine, piperidine, pyrrolidine, benzylamine, α-methylbenzylamine, and the like, for use in converting the compounds of formula SI, when $R^1$ is $CH_2$—monosubstituted phenyl where the substituent is $OSO_3H$, to the corresponding salts. Examples of appropriate inorganic acids for conversion of the compounds of formula SI to the corresponding salts include mineral acids, such as hydrochloric and hydrobromic acids, while appropriate organic acids include trifluoroacetic, ethane disulfonic, or isethionic acids, and the like.

According to Scheme 2, the acylation of compounds of the formula SVII with an electrophylic acylating agent is carried out in an aprotic solvent at temperatures between −30° C. and the boiling point of the solvent, under normal atmospheric pressure, with the exclusion of moisture. If a carbonic acid anhydride, such as acetic anhydride, tert-butyloxycarbonyl-O-phenylmethyl-L-tyrosyl anhydride, $N^α$-tert-butyloxycarbonyl-$N^ε$-phenylmethyloxycarbonylornithyl anhydride or $N^δ$-benzyloxycarbonyl-$N^α$-tert-butyloxycarbonyllysyl anhydride, or a carbonic acid halogenate, such as acetyl chloride or benzyl chloroformate, is used as the electrophylic acylating agent, the reaction is preferably carried out in the presence of an acid binding agent such as a tertiary amine, including triethylamine, pyridine, 4-dimethylaminopyridine and the like, or an alkali metal hydroxide or alkali metal carbonate, including sodium hydroxide, potassium carbonate, and the like. Examples of suitable inert, aprotic solvents include N,N-dimethylformamide, chloroform, methylene chloride, tetrahydrofuran, dioxane, toluene, and chlorobenzene.

The compounds of formula SVI may also be prepared by reacting a compound of formula SVII with an electrophylic acylating agent, such as a carbonic acid, like acetic acid, in an inert solvent at temperatures of from −30° C. to the boiling point of the solvent, preferably at room temperature, in the presence of suitable coupling reagent, such as dicyclohexylcarbodiimide, 1-ethyl-3-(3-dimethylaminopropyl)carbodiimide hydrochloride, carbonyldiimidazole, or the like.

Compounds of the general formula SII may then be obtained by reducing compounds of the general formula SVI by reacting a compound of formula SVI in a protic solvent, such as water, methanol, ethanol, acetic acid, trifluoroacetic acid, and the like, or in an aprotic solvent, like tetrahydrofuran, with a reducing agent, such as sodium cyanoborohydride or lithium, sodium, or potassium borohydride, in a suitable medium, such as acetic acid, trifluoroacetic acid or ethanol, at from −40° to the boiling point of the solvent, for from 5 minutes to 10 hours. Preferably, the reaction is carried out in acetic acid or trifluoroacetic acid at 15° C. for 0.5 hours with sodium cyanoborohydride.

Compounds of the general formula SII may likewise be obtained by a reductive alkylation procedure, whereby the compounds of general formula SVII are dissolved in an acidic medium, preferably acetic acid, with a suitable aldehyde, such as 3-phenylpropanal or carboxylic acid and a reducing agent, preferably sodium cyanoborohydride, at from −10° C. to the boiling point of the acidic medium for from 5 minutes to 60 hours. When the reactant is an aldehyde, the reaction is preferably carried out at room temperature; when the reactant is a carboxylic acid the preferable reaction temperature range is from 55°–60° C.

Pharmaceutically-acceptable salts of the compounds according to the instant invention which have general formula SIIa may then be synthesized from compounds of the general formula SII using methodology described for the preparation of formula SIa compounds.

According to Scheme 3, compounds of the general formula SVIII are produced from compounds of the general formula SX in an acylation reaction using identical methodology described for the preparation of formula SVI compounds.

Compounds of the general formulae SV and SIV may be produced by reducing compounds of respective formulae SX and SVIII by reactions similar to those described for producing compounds of formula SI, with the respective salts of the formulae SV and SIV being produced by methodology as described for the preparation of compounds of the formula SIa.

According to Scheme 4, compounds of the formula SX may be reacted with a suitable electrophylic alkylating agent, such as an alkyl halide, like methyl iodide, alkyl phenyl sulfonate, like ethyl p-toluenesulfonate, alkyl trifluoromethyl sulfonate, like butyl trifluoromethanesulfonate, or the like, in an inert, aprotic solvent in the presence of a suitable base, such as triethylamine, diisopropylethylamine, pyridine, 4-dimethylaminopyridine, sodium hydroxide, potassium carbonate, and the like, to give compounds of the general formula SIX. These reactions may be carried out at from $-30°$ C. to the boiling point of the solvent, preferably at room temperature, for from 1 to 48 hours. The reduction of compounds of the formula SIX to produce compounds of the formula SIII and formation of salts of the formula SIIIa from these compounds may then be accomplished using methodology as described in Scheme 1.

Chiral acylating and alkylating agents of both configurations may be used for the production of analogs of the compounds according to the instant invention. The preferred stereochemical configuration of the products according to the instant invention, however, are those defined in Formula II.

Screening of the novel compounds according to the present invention to determine biological activity and obtain an $IC_{50}$ value for them, in order to identify significant CCK-antagonism, may be accomplished using an $^{125}$I-CCK receptor binding assay and in vitro isolated tissue preparations. These tests involve the following:

CCK receptor binding (pancreas) method

CCK-33 is radiolabeled with $^{125}$I-Bolton Hunter reagent (2000 Ci/mmole), as described by Sankara et al. (*J. Biol. Chem.*, 254, 9349–9351, 1979). Receptor binding is performed according to Innis and Snyder (*Proc. Natl. Acad. Sci.*, 77, 6917–6921, 1980), with the minor modification of adding the additional protease inhibitors, phenyl-methane sulfonyl fluoride and o-phenanthroline, which have no effect on the $^{125}$I-CCK receptor binding assay.

The whole pancreas of a male Sprague-Dawley rat (200–350 g), which has been sacrificed by decapitation, is dissected free of fat tissue and homogenized in 20 volumes of ice-cold 50 mM Tris HCl (pH 7.7 at 25° C.) with a Brinkman Polytron PT-10. The homogenates are centrifuged at 48,000 g for 10 minutes, then the resulting pellets are resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 μl of buffer (for total binding), or unlabeled CCK-8 sulfate sufficient to give a final concentration of 1 μM of CCK-8 (for nonspecific binding), or the compounds of the formula of the compounds according to the instant invention (for determination of antagonism to $^{125}$I-CCK binding) and 25 μl of $^{125}$I-CCK-33 (30,000–40,000 cpm), are added to 450 μl of the membrane suspensions in microfuge tubes. All assays are run in duplicate or triplicate, and the reaction mixtures are incubated at 37° C. for 30 minutes and centrifuged in a Beckman Microfuge (4 minutes) immediately after adding 1 ml of ice-cold incubation buffer. The supernatant is aspirated and discarded, and the pellets are counted with a Beckman Gamma 5000. For Scatchard analysis to determine the mechanism of inhibition of $^{125}$I-CCK binding by the most potent compounds (*Ann. N.Y. Acad. Sci.*, 51, 660, 1949), $^{125}$I-CCK-33 is progressively diluted with increasing concentrations of CCK-33.

CCK receptor binding (brain) method

CCK-33 is radiolabeled and the binding is performed according to the description for the pancreas method, with modifications according to Saito et al., *J. Neurochem.*, 37, 483–490, 1981.

Male Hartley guinea pigs (300–500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkman polytron PT-10. The homogenates are centrifuged at 42,000 g for 15 minutes, then the resulting pellets are resuspended in 80 volumes of binding assay buffer (10 mM N-2-hydroxy-ethylpiperazine-N'-2-ethanesulfonic acid (HEPES), 5 mM $MgCl_2$, 1 mM ethylene glycol-bis-(β-amino-ethylether-N,N'-tetraacetic acid (EGTA), 0.4% BSA and 0.25 mg/ml bacitracin, pH 6.5).

The remainder of the binding assay method is as described for the pancreas method, except that the reaction mixtures are incubated at 25° C. for 2 hours before centrifugation.

An additional method of confirming competitive antagonism of CCK which may be used is the following:

Isolated guinea pig gall bladder method

The two halves of the gall bladders, free of adjacent tissue, of male Hartley guinea pigs (400–600 g), which have been sacrificed by decapitation, are suspended under 1 g tension along the axis of the bile duct in 5 ml organ bath, containing a Kreb's bicarbonate solution of 118 mM NaCl, 4.75 mM KCl, 2.54 $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for 1 hour to obtain equilibrium prior to the beginning of the study and the isometric contractions of the strips are recorded using Statham (60 g:0.12 mm) strain gauges and a Hewlett-Packard 77588 recorder.

CCK-8 is added cumulatively to the baths and $EC_{50}$'s are determined using regression analysis. After washout (every 10 minutes for 1 hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal contractile response, indicates competitive antagonism of CCK from this method.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interactions with dopamine, such as neuroleptic disorders, tardive dyskinesia, Parkinson's disease, psychosis or Gilles de la Tourette Syndrome; and disorders of appetite regulatory systems.

The compounds of the instant invention or pharmaceutically-acceptable salts thereof, may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK in a human subject, the daily dosage will normally be determined by the prescribing physician. Moreover, the dosage will vary according to the age, weight, and response of the individual patient, as well as the severity of the patient's symptoms. In most instances, an effective daily dosage will be in the range of from about 1 mg to about 1500 mg, and preferably, of from 10 mg to about 500 mg administered in single or divided doses. In some cases, however, it may be necessary to use dosages outside these limits.

The invention is further defined by reference to the following examples which are intended to be illustrative and not limiting.

EXAMPLE 1

Preparation of 7,7a-dihydro-7-[(2,3,9,9Aα-tetrahydro-9α-hydroxy-2-(2-methylpropyl)-3-oxo-1H-imidazo(1,2-a)indol-9-yl)methyl]quinazolino(3,2-a)(1,4)benzazepin-5,13-(6H,7H)dione hydrate

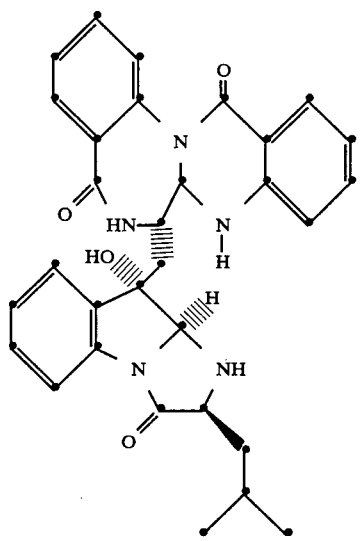

Sodium cyanoborohydride (0.41 grams (6.44 mmol) was added, all at once, to a solution of 1.0 g (1.87 mmol) of 7β-[(2,3,9,9Aα-tetrahydro-9α-hydroxy-2-(2-methylpropyl)-3-oxo-1H-imidazo(1,2-a)indol-9-yl)methyl]-quinazolino-(3,2-A)(1,4)benzazepin-5,13-(6H,7H)dione in 12 ml of glacial acetic acid at 12° C. The reaction was stirred 15 minutes, diluted with 12 ml water, and made basic with saturated $Na_2CO_3$ (ag). The precipitate was removed by filtration, washed thoroughly with water and dried to give the title compound as a white solid (0.85 g, 82% yield):

m.p. 245°–65° C. (shrink); 265°–7° C. (black foam).

TLC: $R_f$, 0.48 (silica GF in 10% MeOH/90% $CH_2Cl_2$).

HPLC: 98% single component.

PMR: according to theory

MS (FAB): 538 (M+ +H), m/e 538).

Elemental analysis for $C_{31}H_{31}N_5O_4 \cdot H_2O$: Calc'd: C,67.01; H, 5.99; N, 12.61. Found: C,67.25; H, 6.04; N, 12.79.

EXAMPLE 2

Preparation of 7-[(1-acetyl-2,3,9,9Aα-tetrahydro-9α-hydroxy-2-(2-methylpropyl)-3-oxo-1H-imidazo(1,2-A)indol-9-yl)methyl]quinazolino(3,2-A)-1,4-benzodiazepin-5,13-(6H,7H)-dione

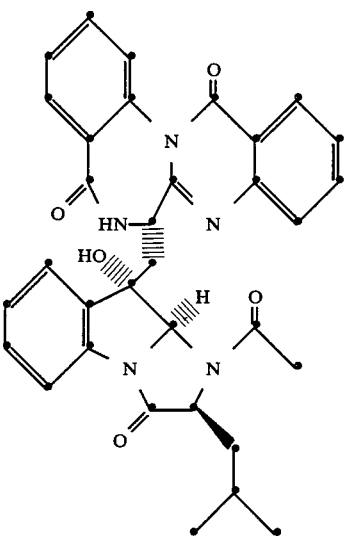

Acetic anhydride (156 μl) and 4-dimethylaminopyridine were added to 2 ml of dry methylene chloride containing 268 mg of 7β-[(2,3,9,9Aα-tetrahydro-9α-hydroxy-2-(2-methylpropyl)-3-oxo-1H-imidazo(1,2-A)indol-9-yl)methyl]quinazolino(3,2-A)-1,4-benzodiazepin-5,13-(6H,7H)-dione. After overnight stirring, the reaction mixture was diluted with methylene chloride to 25 ml, washed with saturated sodium bicarbonate solution and brine, then dried (MgSO$_4$) and concentrated in vacuo. Preparative thick layer chromatography on silica gel (chloroform-methanol 9:1) gave a solid which was recrystallized from ethyl acetate-hexane (50 mg).

m.p. 178°–180° C.

PMR (CDCl$_3$): according to theory.

Elemental Analysis for C$_{33}$H$_{31}$N$_5$O$_5$: Calc'd: N, 12.12; C, 68.62; H, 5.41. Found: N, 12.05; C, 68.42; H, 5.56.

EXAMPLE 3

Preparation of 7-[(1-ethyl-2,3,9,9Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinazolino-(3,2-A)-1,4-benzazepin-5H,13-dione hemihydrate

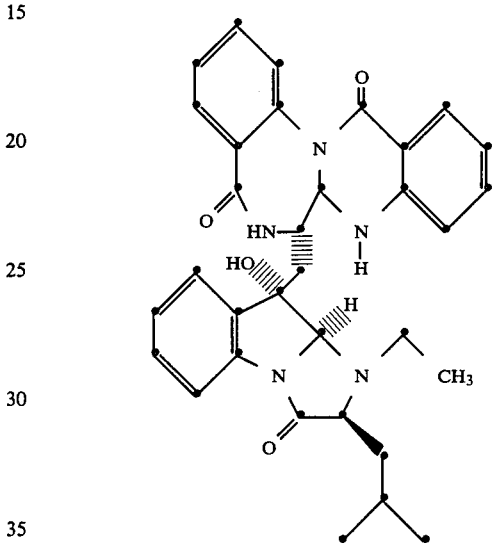

Sodium cyanoborohydride (158 mg (2.52 mmole) was added at room temperature to a solution of 10 ml of acetic acid containing 450 mg (0.84 mmole) of 7β-[(2,3,9,9Aα-tetrahydro-9α-hydroxy-2-(2-methylpropyl)-3-oxo-1H-imidazo(1,2-A)indol-9-yl)methyl]quinazolino(3,2-A)-1,4-benzodiazepin-5,13-(6H,7H)-dione. After two hours, 3 equivalents more of sodium cyanoborohydride were added and the reaction mixture was stirred at 55° C. for 14 hours. The reaction mixture was cooled and poured into 150 ml of water. The resulting precipitate was collected, washed with water and dried; yield: 435 mg. The analytical sample was obtained via silica gel chromatography (95:5 chloroform-ethanol elution) as a white solid (trituration with ether).

PMR (CDCl$_3$): in accord with structure assignment.

Elemental Analysis for C$_{33}$H$_{35}$N$_5$O$_4$.½H$_2$O: Calc'd: N, 12.18; C, 68.97; H, 6.30. Found: N, 11.93; C, 68.98; H, 6.18.

EXAMPLE 4

Preparation of phenylmethyl-2,3,9,9Aα-tetrahydro-9α-hydroxy-2-(2-methylpropyl)-(3-oxo-9-((5,6,7,13-tetrahydro-5,13-dioxoquinazolino(3,2-A)-1,4-benzazepin-7-yl)methyl)-1H-imidazo(1,2-A)indole-1-carboxylate

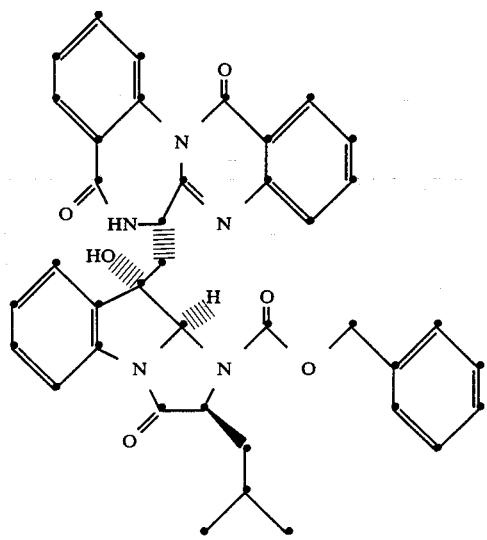

7β-[(2,3,9,9Aα-tetrahydro-9α-hydroxy-2-(2-methylpropyl)-3-oxo-1H-imidazo(1,2-A)indol-9-yl)methyl]-quinazolino(3,2-A)-1,4-benzodiazepin-5,13-(6H,7H)dione (1.0 g, 1.87 mmole) and 4-dimethylaminopyridine (228 mg, 1.87 mmole) were dissolved in 20 ml of dry methylene chloride and the resulting solution was cooled to 0° C. This solution was treated with 1.5 ml (9.25 mmole) of benzylchloroformate and the reaction mixture was allowed to warm to room temperature over 1 hour, before standing overnight. An additional 1.5 ml of benzylchloroformate was added along with 228 mg of 4-dimethylaminopyridine to drive the reaction to completion. After 14 hours, the reaction mixture was diluted with methylene chloride to 400 ml and washed in succession with 10% citric acid (2×50 ml) and brine. The organic phase was dried (MgSO4) and concentrated to give an oil which was further purified by silica gel chromatography (3% ethanol in chloroform) to give the analytical sample as a foam, m.p. 147° C.

PMR (CDCl3): according to theory.

MS (FAB): 670 (M+), 277.

Elemental Analysis for $C_{39}H_{35}N_5O$: Calc'd: N, 10.45; C, 67.94; H, 5.27. Found: N, 9.89; C, 70.87; H, 5.80.

EXAMPLE 5

Preparation of 7,7α-dihydro-7-[(2,3,9,9Aα-tetrahydro-1,9α-dihydroxy-2-(2-methylpropyl)-3-oxo-1H-imidazo-(1,2-A)-indol-9-yl)methyl]quinazolino(3,2-A)-1,4-benzodiazepin-5,13(6H,7H)-dione hydrate

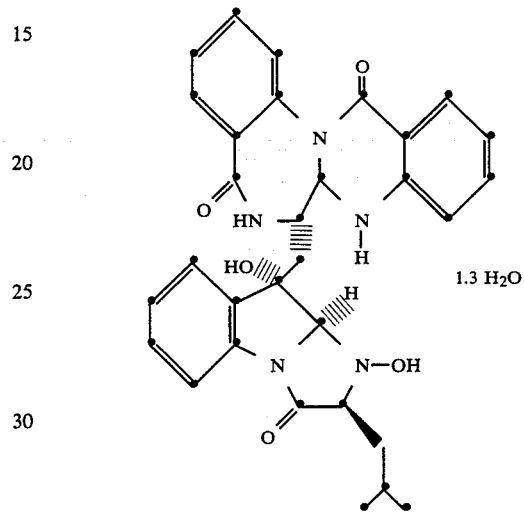

The compound, 7β-[(2,3,9,9Aα-tetrahydro-1,9α-dihydroxy-2-(2-methylpropyl)-3-oxo-1H-imidazo(1,2-A)-indol-9-yl)methyl]quinazolino-(3,2-A)-1,4-benzodiazepin-5,13(6H,7H)-dione (65 mg, 0.118 mmol) was dissolved in acetic acid (0.65 ml) and cooled to 12° C. Sodium cyanoborohydride (25.2 mg, 0.401 mmol) was added to the solution all at once and after stirring 10 minutes, the reaction was diluted with H2O (2 ml), made basic with saturated Na2CO3 solution, and extracted with ethyl acetate (3×10 ml). The combined organic extracts were washed with water and brine, dried over MgSO4, filtered and evaporated to dryness in vacuo at 25° C. (m.p. 206°-29° C., shrink, foam).

Elemental analysis for $C_{31}H_{31}N_5O_5 \cdot 1.3H_2O$: Calc'd: C, 64.52; H, 5.87; N, 12.14. Found: C, 64.63; H, 5.88, N, 12.19.

The compound showed a single spot by TLC ($R_f$=0.26 silica GF, 6% MeOH in CH2Cl2). The PMR spectrum was consistent with the title structure and verified the pressure of water. The compound was 95.0% pure by HPLC.

EXAMPLE 6

Preparation of
7-[1-(3-phenylpropyl)-2,3,9,9Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinazolino(3,2-A)-1,4-benzazepin-5H,13-dione sesquihydrate

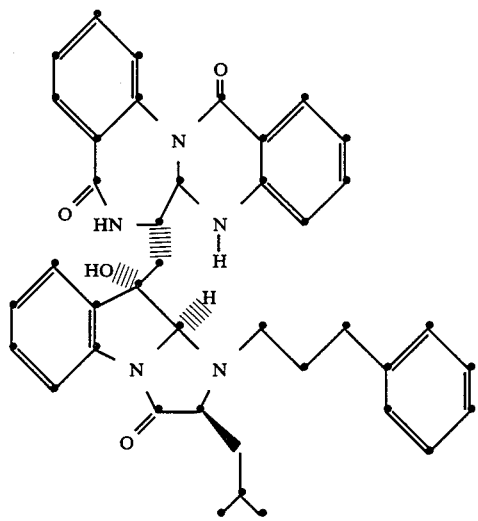

7β-[(2,3,9,9Aα-tetrahydro-9α-hydroxy-2-(2-methylpropyl)-3-oxo-1H-imidazo(1,2-A)indol-9-yl)methyl]-quinazolino(3,2-A)-1,4-benzodiazepin-5,13-(6H,7H)-dione (535 mg, 1 mmole) was dissolved in 10 ml of glacial acetic acid and 3-phenylpropionaldehyde (400 mg, 3 mmole) and sodium cyanoborohydride (504 mg, 8 mmole) were added to this mixture. The reaction was stirred at room temperature for 60 hours and quenched with 75 ml of water. The resulting white precipitate was collected, washed with water and dried; yield 670 mg. The analytical sample was obtained by silica gel chromatography (93:7 chloroform-methanol v/v) as an off-white solid, m.p. 156° C.

MS (FAB): 656 (M+ +H), 377, 292, 249, 204.

PMR (CDCl$_3$): according to theory.

Elemental Analysis for C$_{40}$H$_{40}$N$_5$O$_4$.1.5H$_2$O: Calc'd: N, 10.27; C, 70.46; H, 6.35. Found: N, 10.12; C, 70.76; H, 6.41.

EXAMPLE 7

Preparation of
7-{{1-[N-((1,1-dimethylethoxy)carbonyl)-o-phenylmethyltryosyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione

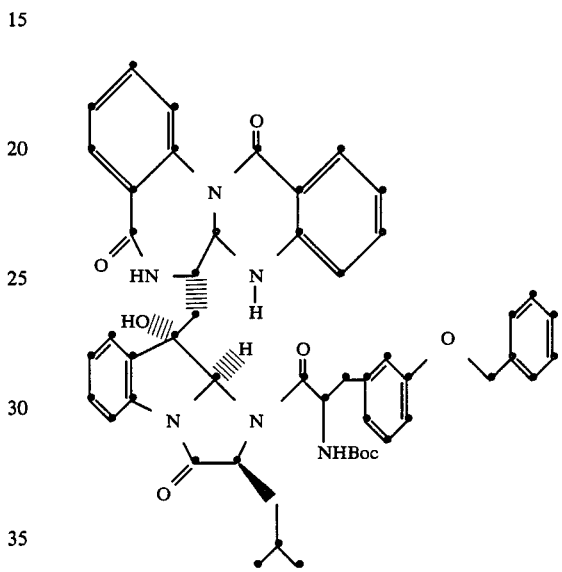

7β-[(2,3,9,9Aα-tetrahydro-9α-hydroxy-2-(2-methylpropyl)-3-oxo-1H-imidazo(1,2-A)indol-9-yl)methyl]-quinazolino(3,2-A)-1,4-benzodiazepin-5,13-(6H,7H)-dione (535 mg, 1 mmole), 4-dimethylaminopyridine (366 mg, 3 mmole), and tert-butyloxycarbonyl-O-phenylmethyl-L-tyrosylanhydride (3.7 g, 5 mmole) were mixed in 20 ml of methylene chloride at room temperature. The reaction mixture was stirred for 16 hours, diluted with 300 ml of ethyl acetate and washed with saturated sodium bicarbonate solution (2×50 ml) and brine. The organic phase was dried (MgSO$_4$) and rotoevaporated to give a semi-solid. Silica gel chromatography (1:1 hexane:ethyl acetate) afforded the analytical sample as an off-white solid; 130° (soften) m.p. 160°.

PMR (CDCl$_3$): according to theory.

MS (FAB): 889 (M+), 597.

Elemental Analysis for C$_{52}$H$_{52}$N$_6$O$_8$: Calc'd: N, 9.45; C, 70.25; H, 5.90. Found: N, 9.55; C, 70.02; H, 6.03.

EXAMPLE 8

Preparation of
7-{{1-[2-((1,1-dimethylethoxy)carbonyl)amino-3-(4-hydroxyphenyl)propanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione hemihydrate

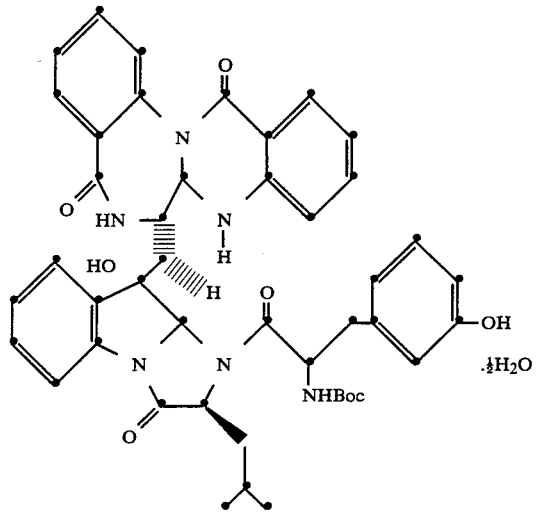

7-{{1-[N-((1,1-Dimethylethoxy)carbonyl)-o-p-henylmethyltyrosyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione (650 mg, 0.73 mmole) was mixed with 300 mg of palladium (10% on carbon) catalyst in 30 ml of ethanol and hydrogenated at 48 psi for 4.5 hours. The reaction mixture was filtered and the filtrate concentrated in vacuo. The resulting oil was chromatographed on silica gel (hexane:ethyl acetate 45:55) to give the analytical sample as a foam; m.p. 163°–169° C.

MS (FAB): 799 (M+ +H), 517, 445, 342.

PMR (CDCl$_3$): according to theory.

HPLC: 95% pure.

Elemental Analysis for $C_{45}H_{46}N_6O_8 \cdot \frac{1}{2}H_2O$: Calc'd: N, 10.40; C, 66.89; H, 5.86. Found: N, 10.15; C, 66.72; H, 6.06.

EXAMPLE 9

Preparation of
7-{{1-[2-((1,1-dimethylethoxy)carbonyl)amino-6-(phenylmethyloxycarbonyl)aminohexanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione hydrate

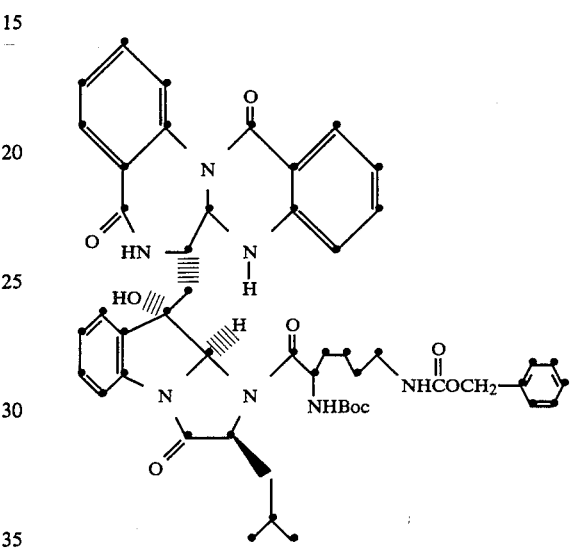

7β-[(2,3,9,9Aα-tetrahydro-9α-hydroxy-2-(2-methylpropyl)-3-oxo-1H-imidazo(1,2-A)indol-9-yl)methyl]-quinazolino(3,2-A)-1,4-benzodiazepin-5,13-(6H,7H)-dione (1.07 g, 2 mmole), 4-dimethylaminopyridine (732 mg, 6 mmole) and $N^\alpha$-tert-butyloxycarbonylamino-N-phenylmethyloxycarbonylaminohexanoic acid anhydride (12.29 g, 16.6 mmole) were combined at room temperature and protected from moisture. After stirring for two hours the reaction mixture was diluted with 600 ml of ethyl acetate and washed with 50% sodium bicarbonate solution and brine. The organic extracts were concentrated and purified via flash chromatography on silica gel (5% ethanol/chloroform elution). The component with $R_f=0.37$ was obtained as a homogeneous product.

PMR (CDCl$_3$): according to theory.

MS (FAB): 898 (M+), 736, 517.

Elemental Analysis for $C_{50}H_{55}N_7O_9 \cdot \frac{3}{4}H_2O$: Calc'd: N, 10.77, C, 65.98; H, 6.28. Found: N, 10.38, C, 66.00; H, 6.40.

EXAMPLE 10

Preparation of
7-{{1-[2-((1,1-dimethylethoxy)carbonyl)amino-5-(phenylmethyloxycarbonyl)aminopentanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione

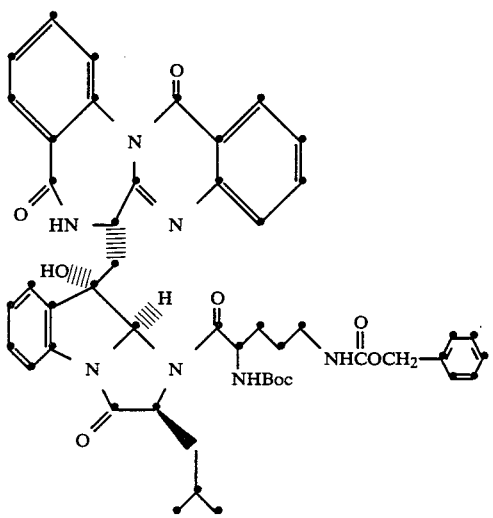

To a solution of 7β-[(2,3,9,9Aα-tetrahydro-9α-hydroxy-2-(2-methylpropyl)-3-oxo-1H-imidazo(1,2-A)indol-9-yl)-methyl]quinazolino(3,2-A)-1,4-benzodiazepin-5,13-(6H,7H)-dione (535 mg, 1.0 mmole) in 15 ml of methylene chloride was added 4-dimethylaminopyridine (122 mg, 1 mmole) and 3.57 g of N$^\alpha$-tert-butyloxycarbonyl(-N-benzyloxycarbonyllysy-lanhydride (5 mmole). The reaction mixture was protected from moisture, stirred for 3 hours and treated with an equivalent quantity of reagents. After 36 hours, the reaction mixture was diluted with ethyl acetate (250 ml) and washed in succession with 10% citric acid solution (2×50 ml), 50% sodium bicarbonate solution (2×50 ml) and brine. The organic phase was dried (MgSO$_4$) and concentrated to yield 3.8 g of a foam. Flash chromatography on silica gel (ethyl acetatehexane, 3:2 then 7:3 v/v) gave the analytically pure product with R$_f$=0.57 as a foam (m.p. 79°–89° C.).

MS (FAB): 884 (M+), 643, 509.

PMR (CDCl$_3$): according to theory.

Elemental Analysis for C$_{50}$H$_{55}$N$_7$O$_9$.¾H$_2$O: Calc'd: N, 10.77; C, 65.98; H, 6.28. Found: N, 10.38; C, 66.00; H, 6.40.

EXAMPLE 11

Preparation of
7-{{1-[2-((1,1-dimethylethoxy)carbonyl)amino-5-(phenylmethyloxycarbonyl)aminopentanoyl]-2,3,9,9Aα-tetrahydro-9α-hydroxy-2-(2-methylpropyl)-3-oxo-1H-imidazo(1,2-A)indol-9-yl}methyl}-6,7,7A,8-tetrahydro-5H,13-quinazolino(3,2-A)-1,4-benzodiazepin-5H,13-dione hydrate

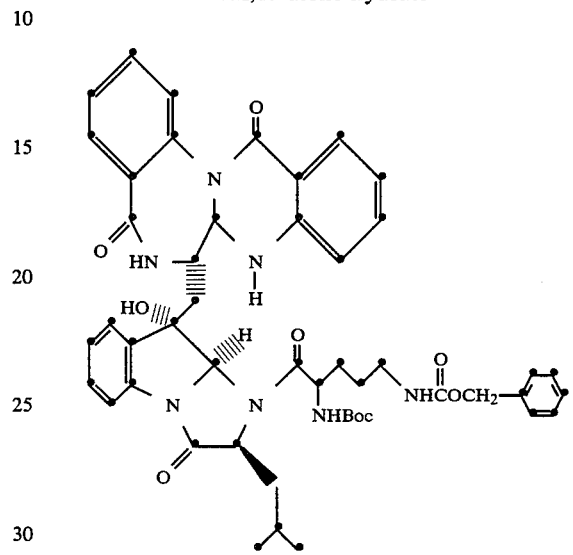

7-{{1-[2-((1,1-Dimethylethoxy)carbonyl)amino-5-(-phenylmethyloxycarbonyl)aminopentanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione (800 mg, 0.90 mmole) and sodium cyanoborohydride (230 mg, 3.6 mmole) were combined with 4 ml of glacial acetic acid at 10° C. After 15 minutes, the reaction mixture was poured into 75 ml of water and the resulting white precipitate was collected and dried (700 mg), m.p. 115° C. (soften), 145° (foam).

PMR (CDCl$_3$): According to theory.

MS (FAB): 886 (M+), 520.

Elemental Analysis for C$_{49}$H$_{55}$N$_7$O$_9$.1.5H$_2$O: Calc'd: N, 10.73; C, 64.45; H, 6.40. Found: N, 10.46; C, 64.79; H, 6.34.

EXAMPLE 12

Activity Testing with I-CCK-8 Pancreas Assay

The compounds of Examples 1–11 were tested as CCK-antagonists (pancreas assay) with the following results:

| Compound from Example | X$^1$ | X$^2$ | X$^3$ | Substituents R | R$^1$ | 7A-8 Bond | Anti-CCK Activity IC$_{50}$ (μM) |
|---|---|---|---|---|---|---|---|
| 1 | H | H | H | H | —CH$_2$CH(CH$_3$)$_2$ | Saturated | 0.21 |
| 2 | H | H | H | O‖—CCH$_3$ | —CH$_2$CH(CH$_3$)$_2$ | Unsaturated | 22 |
| 3 | H | H | H | —CH$_2$CH$_3$ | —CH$_2$CH(CH$_3$)$_2$ | Saturated | 0.35 |
| 4 | H | H | H | O‖—COCH$_2$C$_6$H$_5$ | —CH$_2$CH(CH$_3$)$_2$ | Unsaturated | 5.0 |

-continued

| Compound from Example | X¹ | X² | X³ | Substituents R | R¹ | 7A-8 Bond | Anti-CCK Activity IC₅₀ (μM) |
|---|---|---|---|---|---|---|---|
| 5 | H | H | H | —OH | —CH₂CH(CH₃)₂ | Saturated | 0.67 |
| 6 | H | H | H | —CH₂CH₂CH₂—C₆H₅ | —CH₂CH(CH₃)₂ | Saturated | 0.19 |
| 7 | H | H | H | $-\underset{\underset{NHBoc}{\vert}}{\overset{\overset{O}{\|}}{C}}CH-CH_2-C_6H_4-O-CH_2-C_6H_5$ | —CH₂CH(CH₃)₂ | Unsaturated | 100 |
| 8 | H | H | H | $-\underset{\underset{NHBoc}{\vert}}{\overset{\overset{O}{\|}}{C}}-CH-CH_2C_6H_4-OH$ | —CH₂CH(CH₃)₂ | Unsaturated | 46 |
| 9 | H | H | H | $-\underset{\underset{NHBoc}{\vert}}{\overset{\overset{O}{\|}}{C}}-CH-(CH_2)_4-NH\overset{\overset{O}{\|}}{C}-OCH_2-C_6H_5$ | —CH₂CH(CH₃)₂ | Unsaturated | 100 |
| 10 | H | H | H | $-\underset{\underset{NHBoc}{\vert}}{\overset{\overset{O}{\|}}{C}}-CH-(CH_2)_3-NH\overset{\overset{O}{\|}}{C}OCH_2-C_6H_5$ | —CH₂CH(CH₃)₂ | Unsaturated | 4.3 |
| 11 | H | H | H | $-\underset{\underset{NHBoc}{\vert}}{\overset{\overset{O}{\|}}{C}}-CH-(CH_2)_3-NH\overset{\overset{O}{\|}}{C}OCH_2-C_6H_5$ | —CH₂CH(CH₃)₂ | Saturated | 1.3 |

What is claimed is:

1. Quinazolino-1,4-benzodiazepin-5,13-dione of the formula:

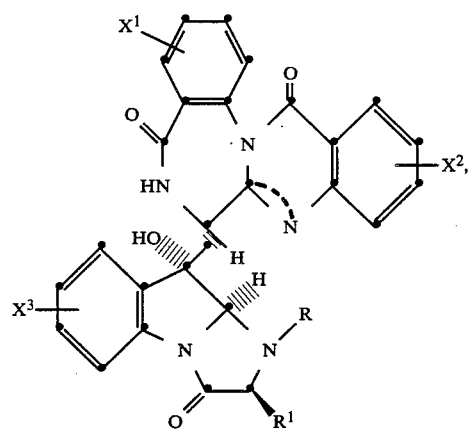

(II)

wherein:

X¹, X² and X³ are independently H, Br, Cl, F, OH, C₁-C₄—alkyl, O—C₁-C₄—alkyl or

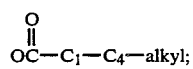

R is H, when the variable bond is a single bond; C₁-C₈—straight- or branched-chain or cyclic alkyl;

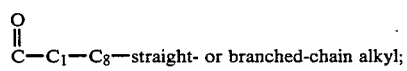

$$\overset{O}{\underset{\|}{C}}-C_3-C_8-\text{cyclic alkyl};$$

$$\overset{O}{\underset{\|}{C}}-C_1-C_8-\text{straight- or branched-chain aralkyl},$$

where the aryl is phenyl or naphthyl, which is unsubstituted or is monosubstituted on the aromatic ring by Br, Cl, F, OH, O—C₁-C₄—alkyl or $$\overset{O}{\underset{\|}{OC}}-C_1-C_4-\text{alkyl}; \overset{O}{\underset{\|}{CO}}-C_1-C_4-\text{alkyl};$$

$$\overset{O}{\underset{\|}{C}}OCH_2-\text{unsubstituted or monosubstituted phenyl or naphthyl,}$$

where the substituent is Br, Cl, F, OH, O—C₁-C₄—alkyl or

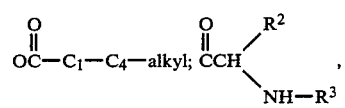

where R² is H; C₁-C₄—straight- or branched-chain alkyl; CH₂—unsubstituted or monosubstituted phenyl, wherein the substituent is Br, Cl, F, OH, O—C₁-C₄—alkyl or

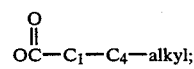

$CH_2$—phenyl—$OCH_2$—phenyl; $CH_2$—3—indole; $CH_2$—imidazole; $CH_2CH_2SCH_3$; $CH_2SCH_2NHCCH_3$;

$CH_2CNH_2$; $CH_2CH_2CNH_2$; $(CH_2)_nNH_2$; or

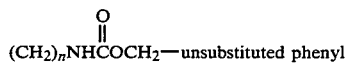
$(CH_2)_nNHCOCH_2$—unsubstituted phenyl wherein n is 1 to 4; and $R^3$ is H,

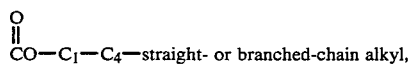
$CO$—$C_1$-$C_4$—straight- or branched-chain alkyl, or

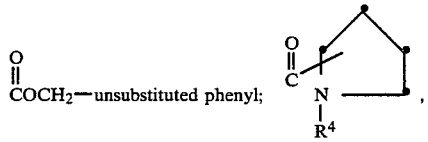
$COCH_2$—unsubstituted phenyl;

where $R^4$ is H,

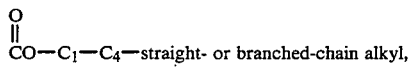
$CO$—$C_1$-$C_4$—straight- or branched-chain alkyl, or

$COCH_2$—unsubstituted phenyl;

$OR^5$, where $R^5$ is $C_1$-$C_8$—straight- or branched-chain or cyclic alkyl;

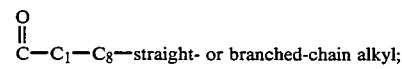
$C$—$C_1$-$C_8$—straight- or branched-chain alkyl;

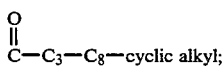
$C$—$C_3$-$C_8$—cyclic alkyl;

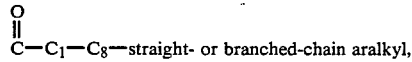
$C$—$C_1$-$C_8$—straight- or branched-chain aralkyl, or branched-chain aralkyl, where the aryl is phenyl or naphthyl, which is unsubstituted or is monosubstituted on the aromatic ring by Br, Cl, F, OH, $C_1$-$C_4$—alkyl, O—$C_1$-$C_4$—alkyl or

$OC$—$C_1$-$C_4$—alkyl; $CO$—$C_1$-$C_4$—alkyl;

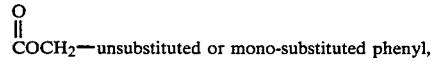
$COCH_2$—unsubstituted or mono-substituted phenyl, where the substituent is Br, Cl, F, OH, O—$C_1$-$C_4$—alkyl or

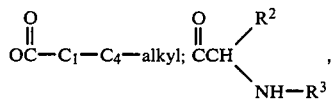
$OC$—$C_1$-$C_4$—alkyl; $CCH$ ... $NH$—$R^3$, where $R^2$ and $R^3$ are as defined above; or

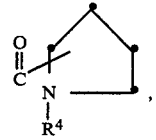

where $R^4$ is as defined above; or OH, when the variable bond is a single bond;
$R^1$ is H, $C_1$-$C_4$—straight- or branched-chain alkyl; $CH_2R^6$, where $R^6$ is hydroxy—$C_1$-$C_4$—alkyl or $CH_2SCH_3$; or unsubstituted or monosubstituted phenyl, where the substituent is OH or $OSO_3H$; and is a single or double bond, or pharmaceutically-acceptable salts of these compounds.

2. A compound according to claim 1, wherein $X^1$, $X^2$ and $X^3$ are H; R is H; OH, when the variable bond is a single bond; $CH_2CH_3$, $CH_2CH_2CH_2$—unsubstituted phenyl;

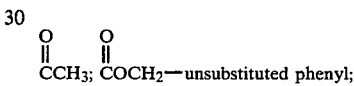
$CCH_3$; $COCH_2$—unsubstituted phenyl;

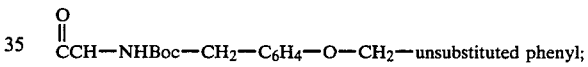
$CCH$—NHBoc—$CH_2$—$C_6H_4$—O—$CH_2$—unsubstituted phenyl;

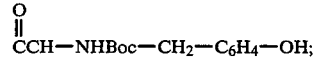
$CCH$—NHBoc—$CH_2$—$C_6H_4$—OH;

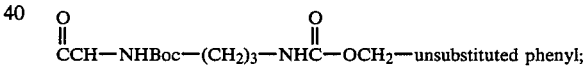
$CCH$—NHBoc—$(CH_2)_3$—NHC—$OCH_2$—unsubstituted phenyl;

or 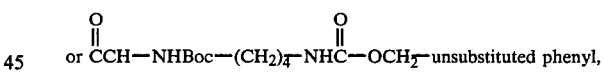 $CCH$—NHBoc—$(CH_2)_4$—NHC—$OCH_2$—unsubstituted phenyl, wherein Boc is tert.-butyloxycarbonyl; and $R^1$ is $CH_2CH(CH_3)_2$, or pharmaceutically-acceptable salts thereof.

3. A compound according to claim 1, wherein $X^1$, $X^2$ and $X^3$ are H; R is H, OH, $CH_2CH_3$ or $CH_2CH_2CH_2$—unsubstituted phenyl; $R^1$ is $CH_2CH(CH_3)_2$; and the variable bond is a single bond, or pharmaceutically-acceptable salts thereof.

4. A compound according to claim 1, selected from: 7,7a-dihydro-7-[(2,3,9,9Aα-tetrahydro-9α-hydroxy-2-(2-methylpropyl)-3-oxo-1H-imidazo(1,2-A)indol-9-yl)methyl]quinazolino(3,2-a)(1,4)benzazepin-5,13-(6H,8H)dione; 7-[(1-acetyl-2,3,9,9Aα-tetrahydro-9α-hydroxy-2-(2-methylpropyl)-3-oxo-1H-imidazo(1,2-A)indol-9-yl)methyl]quinazolino(3,2-A)-1,4-benzodiazepin-5,13-(6H,7H)-dione; 7-[(1-ethyl-2,3,9,9Aα-tetrahydro-9α-hydroxy-2-(2-methylpropyl)-3-oxo-1H-imidazo(1,2-A)indol-9-yl)methyl]6,7,7A,8-tetrahydro-5H,13H-quinazolino(3,2-A)-1,4-benzazepin-5H,13-dione; phenylmethyl 2,3,9,9Aα-tetrahydro-9α-hydroxy-2-(2-methylpropyl)-(3-oxo-9-[(5,6,7,13-tetrahydro-5,13-dioxoquinazolino-(3,2-A)-1,4-benzazepin- 7-yl)methyl]-1H-imidazo-(1,2-A)indole-1-carboxylate; 7,7a-dihydro-7-[(2,3,9,9Aα-tetrahydro-1,9α-dihydroxy-2-(2-methylpropyl)-3-oxo-1H-imidazo-(1,2-A)-indol-9-yl)methyl]-quinazolino(3,2-A)-1,4-benzodiazepin-5,13-(6H,7H)dione; 7-[1-(3-phenylpropyl)-2,3,9,-9Aα-tetrahydro-9α-hydroxy-2-(2-methylpropyl)-3-oxo-1H-imidazo-(1,2-A)indol-9-yl)-methyl]6,7,7A,8-tetrahydro-5H,13H-quinazolino(3,2-A)-1,4-benzazepin-5H,13-dione; 7-{{1-[N-((1,1-dimethylethoxy)-carbonyl)-o-phenylmethyltyrosyl]-2,3,9,9Aα-tetrahydro-9α-hydroxy-2-(2-methylpropyl)-3-oxo-1H-imidazo(1,2-A)-indol-9-yl}methyl}quinazolino-(3,2-A)-1,4-benzodiazepin-5,13-(6H,7H)-dione; 7-{{1-[2-((1,1-dimethylethoxy)carbonyl)amino-3-(4-hydroxyphenyl)propanoyl]-2,3,9,9Aα-tetrahydro-9α-hydroxy-2-(2-methylpropyl)-3-oxo-1H-imidazo(1,2-A)indol-9-yl}-methyl}quinazolino-(3,2-A)-1,4-benzodiazepin-5,13-(6H,7H)-dione; 7-{{1-[2-((1,1-dimethylethoxy)carbonyl)amino-6-(phenylmethyloxycarbonyl)aminohexanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13(6H,7H)-dione; 7-{{1-[2-((1,1-dimethylethoxy)carbonyl)amino-5-(phenylmethyloxycarbonyl)aminopentanoyl]-2,3,9,9Aα-tetrahydro-9α-hydroxy-2-(2-methylpropyl)-3-oxo-1H-imidazo(1,2-A)indol-9-yl}methyl}quinazolino(3,2-A)-1,4-benzodiazepin-5,13-(6H,7H)-dione; and 7-{{1-[2-((1,1-dimethylethoxy)carbonyl)amino-5-(phenylmethyloxycarbonyl)-aminopentanoyl]-2,3,9,9Aα-tetrahydro-9α-hydroxy-2-(2-methylpropyl)-3-oxo-1H-imidazo(1,2-A)indol-9-yl}-methyl}-6,7,7A,8-tetrahydro-5H,13-quinazolino(3,2-A)-1,4-benzodiazepin-5H,13-dione.

5. A compound according to claim 1, selected from: 7,7a-dihydro-7-[(2,3,9,9Aα-tetrahydro-9α-hydroxy-2-(2-methylpropyl)-3-oxo-1H-imidazo(1,2-A)indol-9-yl)methyl]quinazolino(3,2-a)(1,4)benzazepin-5,13-(6H,8H)dione; 7,7α-dihydro-7-[(2,3,9,9Aα-tetrahydro-1,9α-dihydroxy-2-(2-methylpropyl)-3-oxo-1H-imidazo(1,2-A)-indol-9yl)methyl]-quinazolino(3,2-A)-1,4-benzodiazepin-5,13-(6H,7H)-dione; 7-[(1-ethyl-2,3-,9,9Aα-tetrahydro-9α-hydroxy-2-(2-methylpropyl)-3-oxo-1H-imidazo(1,2-A)indol-9-yl)methyl]-6,7,7A,8-tetrahydro-5H,13H-quinazolino(3,2-A)-1,4-benzazepin-5H,13-dione; and 7-[1-(3-phenylpropyl)-2,3,9,9Aα-tetrahydro-9α-hydroxy-2-(2-methylpropyl)-3-oxo-1H-imidazo-(1,2-A)indol-9-yl)-methyl]-6,7,7A,8-tetrahydro-5H,13H-quinazolino(3,2-A)-1,4-benzazepin-5H,13-dione.

6. A process for preparing quinazolino-1,4-benzodiazepin-5,13-dione of formula II:

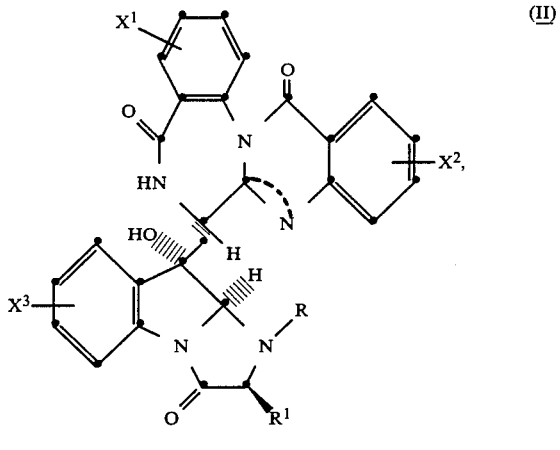

wherein:
$X^1$, $X^2$ and $X^3$ are independently H, Br, Cl, F, OH, $C_1$-$C_4$—alkyl, O—$C_1$-$C_4$—alkyl or

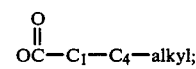

R is H, when the variable bond is a songle bond; $C_1$-$C_8$—straight- or branched-chain or cyclic alkyl;

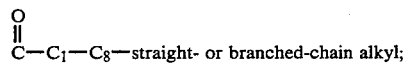

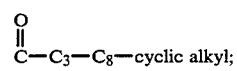

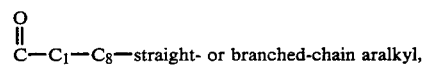

where the aryl is phenyl or naphthyl, which is unsubstituted or is monosubstituted on the aromatic ring by Br, Cl, F, OH, O—$C_1$-$C_4$—alkyl or

where the substituent is Br, Cl, F, OH, O—$C_1$-$C_4$—alkyl or

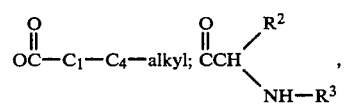

where $R^2$ is H; $C_1$-$C_4$—straight- or branched-chain alkyl; $CH_2$—unsubstituted or monosubstituted phenyl, wherein the substituent is Br, Cl, F, OH, O—$C_1$-$C_4$—alkyl or

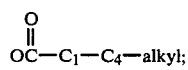

CH$_2$—phenyl—OCH$_2$—phenyl; CH$_2$—3—indole; CH$_2$—imidazole; CH$_2$CH$_2$SCH$_3$;

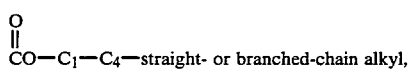

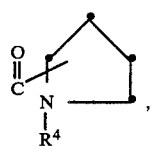

wherein n is 1 to 4; and R$^3$ is H,

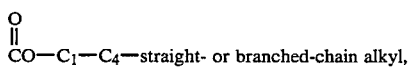

or COCH$_2$—unsubstituted phenyl;

where R$^4$ is H,

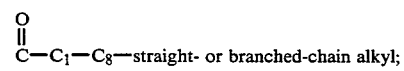

or

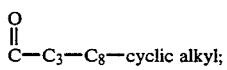

OR$^5$, where R$^5$ is C$_1$-C$_8$—straight- or branched-chain or cyclic alkyl;

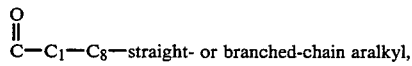

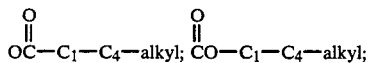

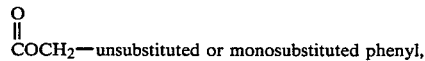

where the aryl is phenyl or naphthyl, which is unsubstituted or is monosubstituted on the aromatic ring by Br, Cl, F, OH, C$_1$-C$_4$—alkyl, O—C$_1$-C$_4$—alkyl or OC—C$_1$—C$_4$—alkyl; CO—C$_1$—C$_4$—alkyl;

COCH$_2$—unsubstituted or monosubstituted phenyl, where the substituent is Br, Cl, F, OH, O—C$_1$-C$_4$—alkyl or

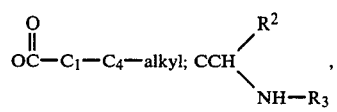

where R$^2$ and R$^3$ are as defined above; or

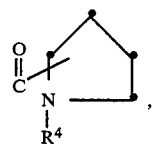

where R$^4$ is as defined above; or OH, when the variable bond is a single bond;

R$^1$ is H, C$_1$-C$_4$—straight- or branched-chain alkyl; CH$_2$R$^6$, where R$^6$ is hydroxy—C$_1$-C$_4$—alkyl or CH$_2$SCH$_3$; or unsubstituted or monosubstituted phenyl, where the substituent is OH or OSO$_3$H; and is a single or double bond, comprising reducing amino compounds of the formula (SVII):

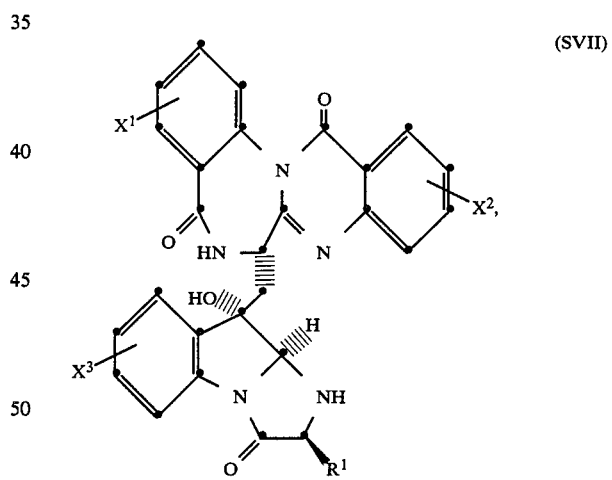

(SVII)

with a suitable reducing agent in a suitable acidic medium; or acylating an amino compound of formula SVII with an electrophilic acylating agent in a suitable aprotic solvent, then reducing the resulting acylated amino compound in an acidic medium with a suitable reducing agent; or dissolving an amino compound of formula SVII in an acidic medium, followed by the addition of a suitable aldehyde and a reducing agent and reaction of these components; or reducing hydroxyamino compounds of the formula (SX):

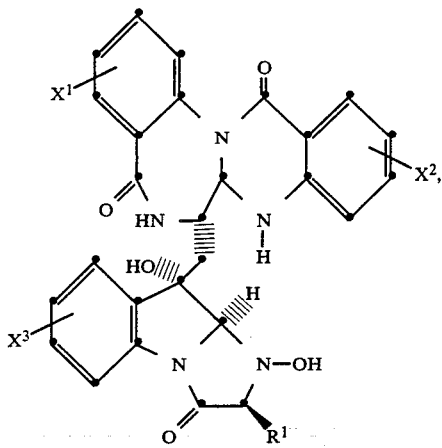

(SX)

with a suitable reducing agent in an acidic medium; or acylating an hydroxy-amino compound of formula SX with an electrophylic acylating agent in a suitable aprotic solvent, then reducing the resulting acylated hydroxy-amino compound in an acidic medium with a suitable reducing agent; or alkylating an hydroxy-amino compound of formula SX with a suitable electrophylic alkylating agent in a suitable aprotic solvent in the presence of a suitable base, then reducing the resulting alkylated hydroxy-amino compound in an acidic medium with a suitable reducing agent.

7. A process according to claim 6, wherein the quinazolino-1,4-benzodiazepin-5,13-dione is suspended in a suitable solvent and reacted with a suitable salt-forming agent.

8. A process according to claim 6, wherein a suitable electrophylic acylating agent is acetyl chloride, acetic acid, benzyl chloroformate, tert-butyloxycarbonyl-O-phenylmethyl-L-tyrosyl anhydride, $N^\epsilon$-benzyloxycarbonyl-$N^\alpha$-tert-butyloxycarbonyllysyl anhydride or $N^\alpha$-tert-butyloxycarbonyl-$N^\delta$-phenylmethyloxycarbonylornithyl anhydride; a suitable electrophylic alkylating agent is methyl iodide, butyl trifluoromethanesulfonate, or ethyl p-toluenesulfonate; a suitable aprotic solvent is N,N-dimethylformamide, chloroform, methylene chloride, tetrahydrofuran, dioxane, toluene or chlorobenzene; a suitable protic solvent is water, methanol, ethanol, acetic acid or trifluoroactic acid; a suitable reducing agent is sodium cyanoborohydride, lithium borohydride, sodium borohydride, or potassium borohydride; a suitable acidic medium is acetic acid or trifluoroacetic acid; a suitable aldehyde is 3-phenylpropanal; and a suitable base is triethylamine, diisopropylethylamine, pyridine, 4-dimethylaminopyridine, sodium hydroxide or potassium carbonate.

9. A process according to claim 7, wherein a suitable solvent is water, methanol, ethanol, ethyl acetate or tetrahydrofuran and a suitable salt-forming agent is sodium hydroxide, potassium carbonate, triethylamine, diisopropylethylamine when $R^1$ is $CH_2R^6$ and $R^6$ is monosubstituted phenyl, where the substituent is $OSO_3H$, or is hydrochloric acid, hydrobromic acid, trifluoroacetic acid, isethionic acid, methanesulfonic acid or ethanedisulfonic acid, when R and $R^1$ are as defined in claim 6, excluding $R^1=CH_2R^6$, wherein $R^6$ is monosubstituted phenyl, where the substituent is $OSO_3H$.

10. A pharmaceutical composition comprising an effective amount for antagonism of the function of cholecystokinins in mammals of one or more quinazolino-1,4-benzodiazepin-5,13-diones or pharmaceutically-acceptable salts of these derivatives, according to claim 1, and a pharmaceutically-acceptable carrier.

11. A pharmaceutical composition according to claim 10, wherein the quinazolino-1,4-benzodiazepine-5,13-diones comprise one or more members of the group consisting of: 7,7a-dihydro-7-[[2,3,9,9a-tetrahydro-9-hydroxy-2-(2-methylpropyl)-3-oxo-1H-imidazo(1,2-A)-indol-9-yl]methyl]quinazolino(3,2-a)(1,4)benzazepine-5,13-(6H, 8H)dione; 7,7α-dihydro-7-[(2,3,9,9Aα-tetrahydro-1,9α-dihydroxy-2-(1-methylpropyl)-3-oxo-1H-imidazo(1,2-A)-indol-9-yl)methyl]-quinazolino(3,2-A)-1,4-benzodiazepine-5,13-(6H,7H)-dione; 7-(1-ethyl-2,3,9,9A-tetrahydro-9-hydroxy-2-(2-methylpropyl)-3-oxo-1H-imidazo(1,2-A)indol-9-yl)-6,7,7A,8-tetrahydro-5H,13H-quinazolino(3,2-A)-1,4-benzazepine-5H,13-dione; and 7-[1-(3-phenylpropyl)-2,3,9,9A-tetrahydro-9-hydroxy-2(2-methylpropyl)-3-oxo-1H-imidazo-(1,2-A)indol-9-yl]-6,7,7A,8-tetrahydro-5H,13H-quinazolino(3,2-A)-1,4-benzazepine-5H,13-dione.

12. A pharmaceutical composition according to claim 10, wherein the effective amount is from about 1 mg to about 1500 mg, administered in single or divided doses.

13. A pharmaceutical composition according to claim 12, wherein the effective amount is from about 10 mg to about 500 mg.

14. A pharmaceutical composition according to claim 10, wherein the mammals are humans.

15. A method of preventing or treating a mammal for disorders of the gastrointestinal, central nervous or appetite regulatory systems which comprises administering to said mammal an effective amount of one or more quinazolino-1,4-benzodiazepine-5,13-diones or pharmaceutically-acceptable salts thereof, according to claim 1.

16. A method according to claim 15, wherein a pharmaceutically-acceptable carrier is also administered.

17. A method according to claim 15, wherein the mamamals are humans and an effective amount is from 1 mg to about 1500 mg, administered in single or divided doses.

* * * * *